US006939301B2

United States Patent
Abdelhak

(12) United States Patent
(10) Patent No.: US 6,939,301 B2
(45) Date of Patent: Sep. 6, 2005

(54) AUTOMATIC VOLUME MEASUREMENTS: AN APPLICATION FOR 3D ULTRASOUND

(76) Inventor: Yaakov Abdelhak, 69 Chester Pl., Apt. 6B, Englewood, NJ (US) 07631

( * ) Notice: Subject to any disclaimer, the term of this patent is extended or adjusted under 35 U.S.C. 154(b) by 116 days.

(21) Appl. No.: 10/100,479

(22) Filed: Mar. 18, 2002

(65) Prior Publication Data

US 2002/0133075 A1 Sep. 19, 2002

Related U.S. Application Data

(60) Provisional application No. 60/276,526, filed on Mar. 16, 2001.

(51) Int. Cl.[7] ................................................ A61B 8/00
(52) U.S. Cl. ....................... 600/437; 600/443; 600/456; 382/128; 382/168
(58) Field of Search ................................ 600/437–472; 382/128, 168, 181–231

(56) References Cited

U.S. PATENT DOCUMENTS 4,341,120 A * 7/1982 Anderson ..................... 73/618
4,996,593 A * 2/1991 Hopkins ..................... 382/147
5,317,417 A * 5/1994 Yamamura et al. ......... 382/194
5,331,442 A * 7/1994 Sorimachi ................... 358/532
5,505,204 A * 4/1996 Picot et al. ................. 600/507
5,588,435 A * 12/1996 Weng et al. ................ 600/443
5,608,849 A * 3/1997 King, Jr. ..................... 345/419
5,812,695 A * 9/1998 Dawe ......................... 382/176
6,312,385 B1 * 11/2001 Mo et al. .................... 600/443
6,434,260 B1 * 8/2002 Soferman et al. ........... 382/131

* cited by examiner

Primary Examiner—Eleni Mantis-Mercader
Assistant Examiner—William Jung

(57) ABSTRACT

A method for determining the volume of an irregularly shaped body part or body such as a fetus using a 3D ultrasonic image composed of light and dark pixels. A caliper is placed on a portion whose volume is to be determined and a computer having the image, automatically counts every pixel with the same echogenicity in every direction as long as it is continuous with the spot the caliper is in, and wherein the computer means stops counting in any direction where the pixels become significantly more echogenic (dark). The volume of the portion, is determined, based on the counted number of pixels and the magnification of the image; and the calculated volume is used to determine physiological characteristics based on known values such as fetal gestation age.

3 Claims, No Drawings

AUTOMATIC VOLUME MEASUREMENTS: AN APPLICATION FOR 3D ULTRASOUND

This application claims benefit of Provisional appln No. 60/276,526 filed Mar. 16, 2001.

FIELD OF THE INVENTION

This invention relates to ascertaining gestation volume and weight of fetuses at various times during a pregnancy by means of 3D ultrasound measurement, with accurate monitoring of fetal development and gestational age.

BACKGROUND OF THE INVENTION

As described in detail at internet site, www.obultrasound-.net (the contents of which site is included herein by reference thereto), obstetric ultrasound is the use of ultrasound scans in pregnancy. Since its introduction in the late 1950's ultrasonography has been used as a diagnostic tool in obstetrics. Currently used equipment comprises real-time scanners, with which a continuous picture of the moving fetus is depicted on a monitor screen. Very high frequency sound waves of between 3.5 to 7.0 megahertz (i.e. 3.5 to 7 million cycles per second) are generally used for this purpose. They are emitted from a transducer which is placed in contact with the maternal abdomen, and which is moved to "look at" any particular content of the uterus. Repetitive arrays of ultrasound beams scan the fetus in thin slices and are reflected back onto the same transducer. The information obtained from different reflections is recomposed back into a picture on the monitor screen as a sonogram, or ultrasonogram. Movements such as fetal heart beat and malformations in the fetus can be assessed and measurements are often made based on the images displayed on the screen and such measurements are the most common in the assessment of gestational age, size and growth in the fetus.

Determination of Gestational Age and Assessment of Fetal Size:

Fetal body measurements reflect the gestational age of the fetus. This is particularly true in early gestation. In patients with uncertain last menstrual periods, such measurements must be made as early as possible in pregnancy to arrive at a correct dating for the patient. In the latter part of pregnancy, measuring body parameters will still allow for assessment of the size and growth of the fetus but with reduced accuracy.

The accuracy of ultrasound for dating a pregnancy depends on at what point during the pregnancy the ultrasound is taken. Pregnancy dating is most accurate during the first eighteen weeks of pregnancy. Measurement of the sac at five to seven weeks is not accurate.

The following measurements are usually made, based on ultrasonic scans:

a) The Crown-rump Length (CRL)

This measurement can be made between 7 to 13 weeks and provides a relatively accurate estimation of the gestational age. Dating with the CRL can be within 3-4 days of the last menstrual period. Measuring the crown-rump length gives an accuracy of plus or minus three days at seven weeks and this test can be appropriately used from the seventh to the fourteenth week.

Between thirteen and twenty-six weeks, measurements of the biparietal diameter, the femur length and abdominal circumference, are generally used. The accuracy is plus or minus seven to ten days and the accuracy further declines with advancing gestation age:

b) The Biparietal Diameter (BPD)

This is the diameter between the 2 sides of the head and it is measured after 13 weeks. It increases from about 2.4 cm at 13 weeks to about 9.5 cm at term. Different babies of the same weight can have different head size, therefore dating by this parameter, in the later part of pregnancy, is generally considered unreliable.

c) The Femur Length (FL)

The femur is the longest bone in the body and reflects the longitudinal growth of the fetus. Usefulness of this parameter is similar to that of the BPD. It increases from about 1.5 cm at 14 weeks to about 7.8 cm at term.

d) The Abdominal Circumference (AC)

This is the single most important measurement to make in late pregnancy. It reflects more of fetal size and weight rather than age. Serial measurements are useful in monitoring growth of the fetus.

The weight of the fetus at any gestation can also be estimated with some accuracy using polynomial equations containing the BPD, FL, and AC. Lookup charts are readily available. For example, a BPD of 9.0 cm and an AC of 30.0 cm will give a weight estimate of 2.85 kg.

The above measurements are generally based on 2D ultrasound scans as determined with the utilization of measuring calipers.

Other useful parameter measurements include:

e) Gestational Sac Diameter (GS)

The gestational sac can be visualized as early as 4.5 weeks. It increases by about 1 mm per day. As the sac is not usually round, an average of the length, width and depth is made. The accuracy of dating using GS size is low and can be off by a whole week. This is therefore not recommended. Fetal crown-rump length should be used wherever possible for dating a pregnancy.

f) Yolk Sac Diameter (YS)

Before placental circulation is established, the yolk sac is the primary source of exchange between the embryo and the mother. Between 7 and 11 weeks, the YS can reach a diameter of up to 7 mm, after which it will decrease in size. Absence of the YS in the presence of an embryo is always abnormal and is associated with fetal demise. A larger than normal YS is also associated with adverse outcome in the fetus. In general a YS diameter of greater than 5.6 mm before 10 weeks is likely to be associated with abnormal fetal outcome.

g) Head Circumference (HC)

The head circumference is used similar to the BPD for dating. It is supposed to be better than the BPD because it compensates for the shape of the fetal head (for example, a very flat head will give a smaller BPD). However the measurement itself is technically more difficult to make and carries with it a higher degree of measurement error. Its use is valuable in fetuses with abnormal head shape.

Another measurement, the Cephalic Index, has a similar function. It is the ratio between the two axis of the fetal head. A value of under 74% represents an excessively flat head.

h) The Nuchal Skin Fold

The nuchal skin fold is increased in cases where skin oedema is present. And this occurs in Turner's syndrome, Down's syndrome and a number of chromosomal abnormalities. Between 10 to 13 weeks, the normal nuchal fold is less than 3 mm and after 16 weeks it should not exceed 6–7 mm.

i) Other Long Bone (Limb) Measurements

Charts for other long bones in the fetal body are all available, such as for the humerus, radius, ulnar, tibia and fibula. These are important mainly in the diagnosis of congenital malformations and not so much as in the assessment of gestational age of the fetus.

j) Other Measurements

Normal values for many other fetal body measurements are available, such as sizes for the cerebellum, heart chambers, ear, kidneys, and lengths of the foot, clavicles or distances between two orbits etc. These are useful when assessing certain fetal anomalies in which a particular part of the fetus is known to be affected.

k) Morphometric Ratios

Ratios of the Head circumference to the Abdominal circumference (HC/AC ratio)and of the Femur length to Abdominal circumference (FL/AC ratio) are often used to assess fetal growth. As the AC tends to shrink more in fetal growth retardation, the ratios may be helpful in situations when a dating scan is not available. On the other hand, results from such ratios may be misleading as for example the ratio may appear normal in a growth-retarded fetus when both the limbs and the abdomen are affected to such a degree that both are shrunken.

A refinement of two dimensional (2D) ultrasound, the three dimensional (3D) ultrasound is quickly moving out of the research and development stages and faster and more advanced commercial models are coming into the market. The scans require special probes and software to accumulate and render the images, and the rendering time has been reduced from minutes to seconds. Advantages of the 3D ultrasound images include enhanced discernment and diagnosis of defects and even small defects such as spina bifida, cleft lips/palate, and polydactyl. Other more subtle features such as low-set ears, facial dysmorphia or clubbing of feet can be better assessed, leading to more effective diagnosis of chromosomal abnormalities. However, measurements and gestational age estimations has not been enhanced thereby to date.

A 3D sonogram machine, the Combison 530 (Kretztechnik, Austria) has been commercially available for some time. It employs an abdominal and vaginal Voluson sector transducer (3.5/5.0 MHz). It allows selection of orthogonal planes at any orientation and position. This system can provide a clear 3-dimensional surface rendering or a transparency view of fetal structures, within a few seconds.

The following is an excerpt from a paper entitled: Volume scanning in the evaluation of fetal malformations: a new dimension in prenatal diagnosis by E. Merz, F. Bahlmann and G. Weber from the Gutenberg University at Mainz, Germany, appearing in the journal "Ultrasound in Obstetrics and Gynecology" Volume 5 pp. 222–227, 1995 (as excerpted on said web site):

The abdominal Voluson sector transducer is a 90 mechanical annular array transducer with a relatively large coupling area. Its fast scan sector is swept automatically in a direction perpendicular to the fast scan plane.

The three-dimensional investigation is performed in a similar manner to the conventional two-dimensional ultrasound examination. After the field of interest is targeted with a volume box in the normal two-dimensional scan, a volume scan can be activated, causing the transducer inside the transducer housing automatically to sweep 40 with 4 s in the normal velocity mode. By this volume scan, the data set from a pyramid-shaped tissue volume is acquired. The complete data set is stored in the Combison random-access memory (RAM). In the stored volume, a set of precisely equally spaced sector scans can be reviewed simultaneously in the three dimensions, producing tomographic images.

Depending on the volume size and data acquisition time, different numbers of scans are available. In the longitudinal section, a maximum of 256 scans are accessible and can be displayed. In the transverse section, and in the frontal or coronal section (parallel to the abdominal wall), a maximum of 1024 scans can be displayed.

For surface reconstruction, the volume can be rotated in a dimension such that the fetus or the organ of interest is directly facing the examiner. Disturbing factors such as the placenta, the arm or leg of the fetus or the umbilical cord can be eliminated by "Cartesian storing", where only the most interesting part of the volume is stored. After the selection of such a volume of interest, unwanted small echo signals can be suppressed with the lower threshold. The view angle and the number of the three-dimensional reconstructions are then defined. A 3D image in the surface mode is available for review after a data processing time of 8–20s, depending on the volume size. The reconstruction of a translucency view takes the same time, but there is no necessity to reduce the small echo signals.

After reconstruction of several views from various angles, the object can be rotated on the screen to provide a better representation of spatial geometry.

Archival storage of data is accomplished with removable cartridge hard disks (SyQuest) with 88 Mbyte capacity.

An advantage of the 3D image is that the examiner has a complete overview of the field of interest, with all three orthogonal planes (sagittal, transverse and frontal) being simultaneously viewable on the screen, thereby allowing an exact identification of anatomical planes for biometry as well as precise volume measurements.

Frontal planes parallel to the abdominal wall are also visible. These views are not available with conventional ultrasound. For slice orientation relative to the patient's anatomy, a framework is displayed simultaneously with the orthogonal planes.

Because of the large memory, the stored volume can be dissected millimeter by millimeter in all three dimensions, allowing post-scan tomographic examination. Surface and transparent images can be calculated and displayed directly by the ultrasound unit within a few seconds. The surface image gives a sculpture-like impression of the fetus; the transparent view shows clear skeletal details similar to a postnatal X-ray.

Transfer of data onto hard disks allows degradation-free storage of the complete data sets and any stored volume can be reviewed at any time by the same examiner or by another person. Any plane can be re-analyzed and any distance can be re-measured.

In operation, high frequency ultrasound is widely used in medical imaging for the evaluation of a patient's internal organs. Ultrasound waves are transmitted into the patient's body where the waves are propagated through the internal organs. Each tissue has differences in density, elasticity, and stiffness, which affects the speed at which the ultrasound waves travel through them. A sensor, utilizing a piezoelectric element collects the reflected ultrasound waves and converts the mechanical energy to electrical energy. The electrical energy is then used to form a visual image of the studied structure.

Ultrasound imaging has progressed over the last thirty-five years. Initially, A mode was developed which provided an amplitude-modulated display of the returning echoes. B mode advanced the imaging by assigning a brightness-modulated display to the returning signal. Ultrasound waves that were reflected off denser, less elastic tissue such as bone would be assigned a bright spot on the image. At the other end of the spectrum, fluids, which transmitted and reflected sound slower were assigned a dark spot (echolucent pixels) on the display.

Real time imaging was developed which really is multiple static images (B mode) updated every fraction of a second to produce a frame rate, which appears to be continuous. Using this technology an ultrasonographer can find correct image planes on a patient and freeze the picture. Structures can then be measured in length by placing calipers from one point to a second. This is the system currently employed in determining size of fetal structures. Using nomograms, these measurements are determined to be normal or abnormal. To determine an approximate volume of a structure multiple measurements are carried out and standard calculations are used for an approximate volume. This estimate is only possible when assessing a regularly shaped structure such as a sphere.

Recently, as described above, 3D ultrasound has been introduced. Integration of successive and close planes is performed so that a volume is constructed. This technology has been used to render three-dimensional images that allow better appreciation of fetal structural anomalies. That is when a fetal anomaly is suspected after 2D real time scanning, a 3D ultrasound is done collecting a volume rendering of the studied structure. At this point, this limited use of 3d ultrasound has prevented it from wide use in medical imaging.

SUMMARY OF THE INVENTION

It is an object of the present invention to provide a more reliable and accurate method for determining gestation age of a fetus by means of 3D ultrasound imaging.

It is a further object of the present invention to automatically determine the substantially exact volume of a fetus by means of an artifact of said imaging and using said volume to determine gestation age and other diagnostic elements relative to fetus development.

These and other objects, features and advantages of the present invention will become more evident from the following discussion.

Generally the present invention comprises a method for accurately automatically measuring the volume of 3D ultrasound images of a body or body part and particularly that of a fetus during gestation, whereby after a 3D ultrasound image is collected, a sonographer can obtain a volume measurement of a cystic structure by simply placing the caliper in the area in the image of interest. Said method for obtaining the volume of a body or body part and particularly the body or body part of an inaccessible and irregularly shaped fetus comprises the steps of:

a) obtaining a three dimensional (3D) ultrasound image of said body or body part as a series of light and dark pixels stored by computer means;

b) placing portion defining means, such as a caliper, on a portion of the image for which the volume is desired, wherein the portion defining means is linked to the computer means to thereby define the portion;

c) programming the computer means to controllably count or tally the amount of echolucent (dark) pixels that are continuous with that area, whereby the computer means counts every pixel with the same echogenicity (plus or minus a correction range determined by the resolution of the image) in every direction as long as it is continuous with the spot the caliper is in, and wherein the computer means stops counting in any direction where the pixels become significantly more echogenic (dark), and effecting said controlled counting;

d) calculating a volume of said portion, based on the counted number of pixels and the magnification of the image; and e) using the calculated volume to determine physiological characteristics based on known values.

Thus, for determination of fetal gestation age, the volume is correlated to a weight, with specific known fetal weights being directly accurately correlated to fetal weights at specific gestation ages.

The present method is more accurate then currently employed length measurements and is just as easily applied to any irregularly shaped structures.

Examples of the use of the volume determination method of the present invention in the field of obs/gyn include in a non-limiting way determination of the volume of ovary volume and ovarian mass; fetal pole volume in early pregnancy for early pregnancy dating; fetal heart chambers; fetal kidneys; fetal bladder; fetal brain structures; fetal head ventricle; fetal extremity volume as a reflection of fetal weight; fetal nuchal translucency volume in assessing for risk of trisomy 21; fetal hydronephrosis; and amniotic fluid volume.

DETAILED DESCRIPTION OF THE PRESENT INVENTION

In order to more clearly illustrate the efficacy of the present invention the following example is presented. It is however understood that such examples are merely exemplary of the present invention and are not considered to be limitations on the present invention.

Examples of Applications Using 3D Ultrasound Volume Estimates

EXAMPLE

A patient presents in the first trimester of pregnancy. She is unsure of her last menstrual period and a due date needs to be assigned. Normally, a 2D ultrasound of the fetal pole is obtained and the measurement of the long axis of the fetus (crown rump length) is used to give the estimated fetal age. This is generally accurate to within one week. Using volumetric measurements, as described, fetal volume, and hence weights, are automatically computed via 3D scanning. This method has the advantage of being much more accurate and will be more precise in the estimate of the gestational age. A second advantage is the automation removes the subjectivity of caliper placements by the sonographer. The following are comparative volume and fetal gestation age determinations:

A) Fetal pole length=30 mm=10 weeks+7 days

B) Volume estimate=35.0 cc=35.0 grams=10 weeks gestation±1 day

Measurements of the fetal 'nuchal translucency' between 11 and 14 weeks are regularly used as a screening test in assessing the risk of Trisomy 21. Fluid between the fetal spine and the fetal skin at the level of the fetal neck is a normal phenomenon seen in early fetal development. This fluid is in a confined and well-circumscribed place. It is well documented that an excess of fluid in this space is associated with a significant risk of Trisomy 21. Currently, using 2D ultrasound the fluid amount is estimated by an anterior-posterior diameter measurement at the level of the fetal neck. This is a tedious process since the image has to be captured with the fetus in a perfectly sagital lie, a time consuming process. The fetus must also be in a neutral position. Fetal body flexion will decrease this diameter and extension will increase it. Moreover, the placement of the calipers must be exactly along the edge of the skin/fluid line.

To avoid inter-observer differences and limit technical errors in the measurement, all providers using this screening method are required to take a nuchal translucency certification course and exam. Using 3D volumetric measurement negates all of these problems. The fetal image is captured as a complete volume and no specific sagital image is required. Fetal flexion or extension does not affect the inter-nuchal fluid volume. The computer automatically determines the nuchal-fluid borders thereby avoiding subjective caliper placement.

When a fluid filled cyst is noted in the pelvis. The size is usually determined by taking captured images along the X, Y, and Z, axis and measuring the widest diameter of the cyst. Follow-up scans are performed to determine if the cyst has enlarged. This is a very rough estimate. Cysts are not perfectly round and the widest diameter of each axis may not reflect the actual size of the cyst. Automated volume measurements in accordance with the present invention allows much more precise determinations of the cyst size in both round and non-spherical cysts. Follow up scans will be much more sensitive in diagnosing cyst growth.

It is understood that the above are exemplary of the present invention and that changes may be made to the procedure of the present invention and the particular body part volumes without departing from the scope of the present invention as defined in the following claims.

What is claimed is:

1. A method for obtaining the volume of a body or body part comprising the steps of:
   a) obtaining a three dimensional (3D) ultrasound image of said body or body part as a series of light and dark pixels stored by computer means;
   b) placing portion defining means, on a portion of the image for which the volume is desired, wherein the portion defining means is linked to the computer means to thereby define the portion;
   c) programming the computer means to controllably count the amount of pixels that are continuous with that portion, whereby the computer means counts every pixel with the same echogenicity in every direction as long as it is continuous with the spot the caliper is in, and wherein the computer means stops counting in any direction where the pixels become significantly more echogenic (dark); and effecting said controlled counting;
   d) calculating a volume of said portion, based on the counted number of pixels and the magnification of the image; and
   e) using the calculated volume to determine physiological characteristics based on known values.

2. A method for obtaining the volume of a body or body part comprising the steps of:
   a) obtaining a three dimensional (3D) ultrasound image of said body or body part as a series of light and dark pixels stored by computer means;
   b) placing portion defining means, on a portion of the image for which the volume is desired, wherein the portion defining means is linked to the computer means to thereby define the portion;
   c) programming the computer means to controllably count the amount of pixels that are continuous with that portion, whereby the computer means counts every pixel with the same echogenicity in every direction as long as it is continuous with the spot the caliper is in, and wherein the computer means stops counting in any direction where the pixels become significantly more echogenic (dark); and effecting said controlled counting;
   d) calculating a volume of said portion, based on the counted number of pixels and the magnification of the image; and
   e) using the calculated volume to determine physiological characteristics based on known values, wherein said volume is a fetus or portion thereof and wherein said volume of said portion is correlated to a known weight for said fetus or portion thereof as a function of gestation age to thereby determine said gestation age.

3. The method of claim 2 wherein said volume is one of ovary volume and ovarian mass; fetal pole volume in early pregnancy for early pregnancy dating; fetal heart chambers; fetal kidneys; fetal bladder; fetal brain structures; fetal head ventricle; fetal extremity volume as a reflection of fetal weight; fetal nuchal translucency volume in assessing for risk of trisomy 21; fetal hydronephrosis; and amniotic fluid volume.

* * * * *